(12) United States Patent
Natori et al.

(10) Patent No.: US 9,877,636 B2
(45) Date of Patent: Jan. 30, 2018

(54) INSERTION APPARATUS

(71) Applicant: OLYMPUS CORPORATION, Tokyo (JP)

(72) Inventors: Yasuaki Natori, Akishima (JP); Fumiyuki Onoda, Tama (JP); Keijiro Omoto, Hachioji (JP); Takashi Yamashita, Hachioji (JP); Takashi Suzuki, Hino (JP); Yoshitaka Umemoto, Hachioji (JP); Takuro Onda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/602,490

(22) Filed: May 23, 2017

(65) Prior Publication Data

US 2017/0251909 A1    Sep. 7, 2017

Related U.S. Application Data

(63) Continuation of application No. PCT/JP2016/060473, filed on Mar. 30, 2016.

(30) Foreign Application Priority Data

Apr. 1, 2015    (JP) ................................. 2015-075410

(51) Int. Cl.
*H02P 5/00* (2016.01)
*A61B 1/00* (2006.01)
(Continued)

(52) U.S. Cl.
CPC ........ *A61B 1/00108* (2013.01); *A61B 1/0057* (2013.01); *A61B 1/00133* (2013.01); *A61B 1/04* (2013.01); *H02P 23/14* (2013.01)

(58) Field of Classification Search
USPC .................................................. 318/430–434
See application file for complete search history.

(56) References Cited

U.S. PATENT DOCUMENTS 6,159,208 A * 12/2000 Hovda ............... A61B 18/1485
                                                           128/898
6,264,650 B1 * 7/2001 Hovda ................. A61B 18/148
                                                           604/114
(Continued)

FOREIGN PATENT DOCUMENTS

| JP | 2008-93029 A | 4/2008 |
| JP | 2011-172776 A | 9/2011 |
| JP | 2014-64686 A | 4/2014 |

OTHER PUBLICATIONS

International Search Report dated Jun. 14, 2016 received in PCT/JP20161060473.

(Continued)

*Primary Examiner* — Bentsu Ro
(74) *Attorney, Agent, or Firm* — Scully, Scott, Murphy & Presser, P.C.

(57) ABSTRACT

An insertion apparatus includes an insertion section, a motor that rotates a rotational housing, a drive control unit that supplies a driving current to the motor to control driving of the motor, a driving current detector that detects the driving current flowing through the motor, a torque limit value storage unit that stores a torque limit value, a temperature detector detects a temperature of the rotational housing, a temperature measurement unit that measures a temperature in a vicinity of the rotational housing based on a detection result obtained from the temperature detector, and a torque limit value correction unit that corrects the torque limit value in accordance with the temperature measured by the temperature measurement unit.

6 Claims, 4 Drawing Sheets

(51) Int. Cl.
*A61B 1/04* (2006.01)
*A61B 1/005* (2006.01)
*H02P 23/14* (2006.01)

(56) References Cited

U.S. PATENT DOCUMENTS 9,522,003 B2 * 12/2016 Weir ................ A61B 17/07207
2008/0086029 A1   4/2008 Uchiyama et al.

OTHER PUBLICATIONS

English translation of the Written Opinion of the International Searching Authority from International Application No. PCT/JP2016/060473 dated Aug. 21, 2017.

* cited by examiner

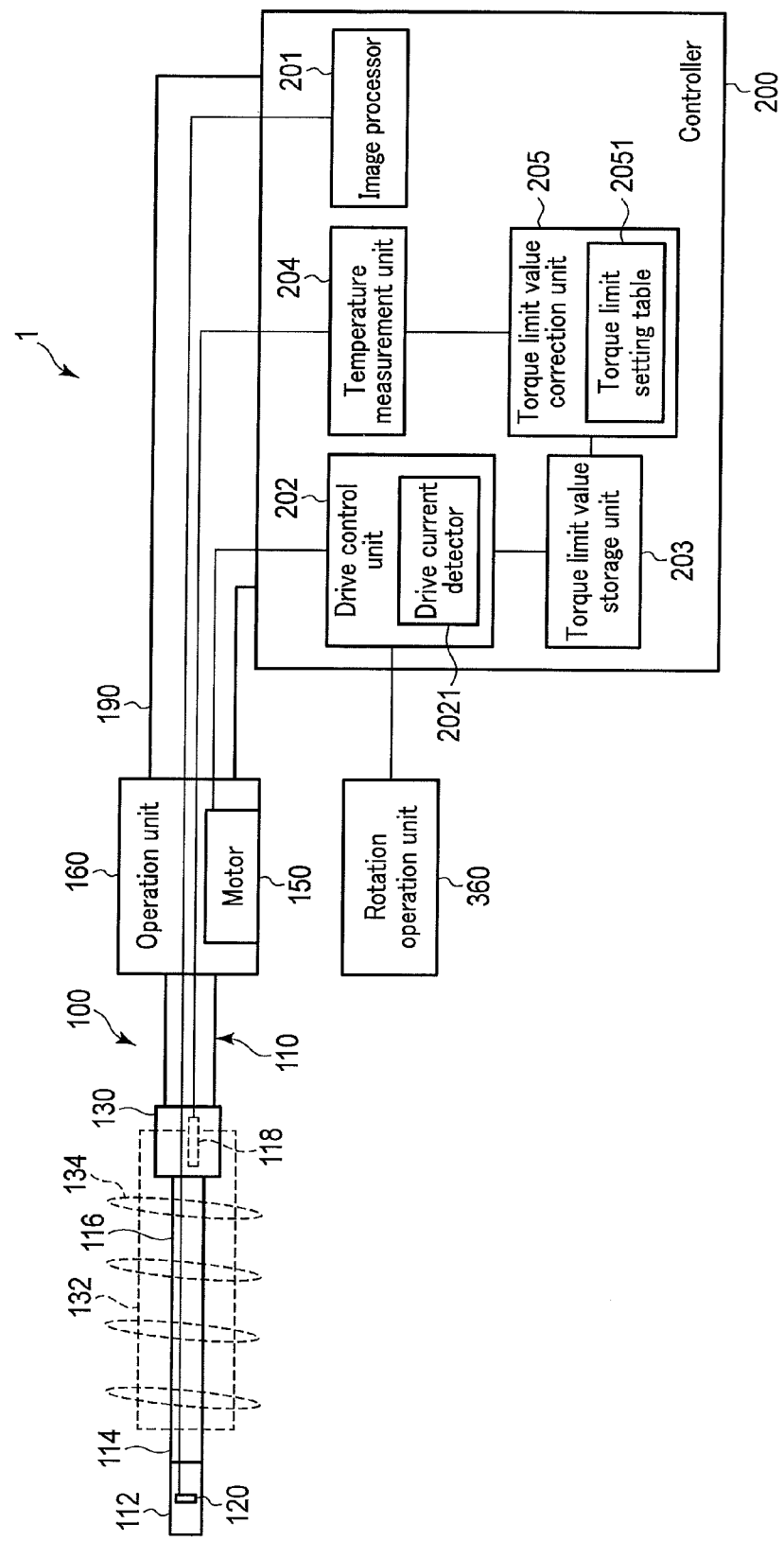
F I G. 1

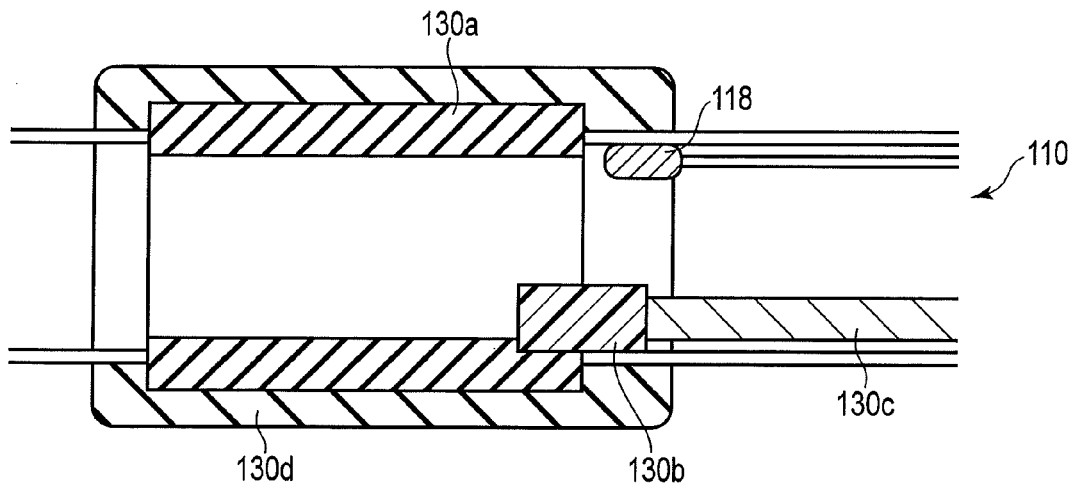
F I G. 2
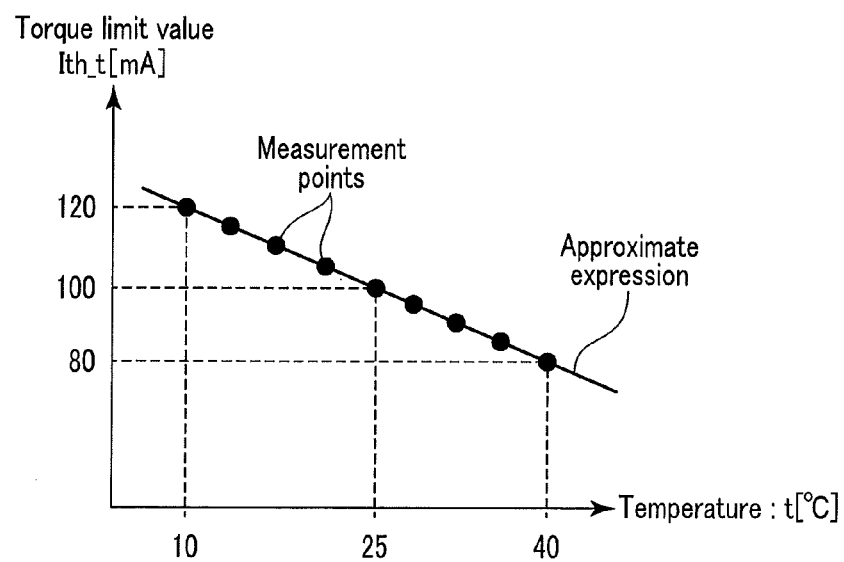
F I G. 3

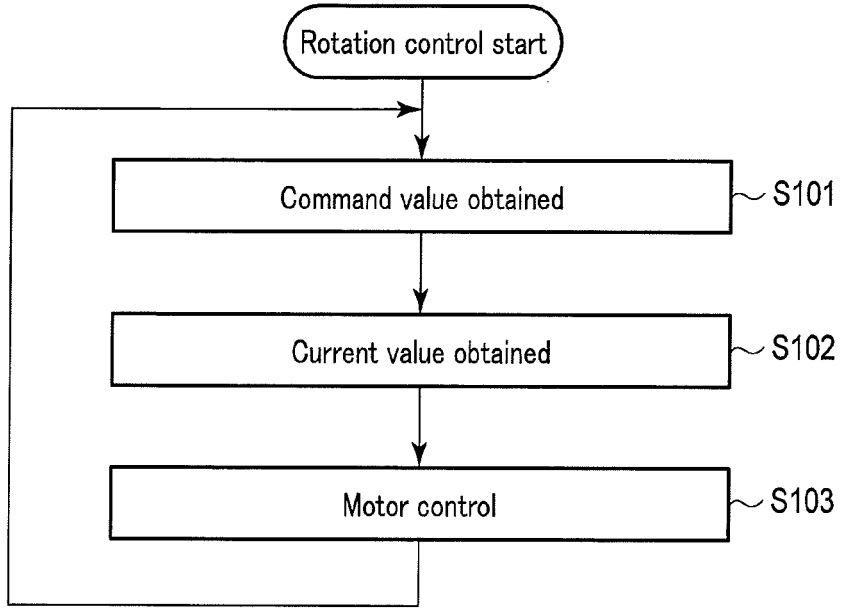
F I G. 4
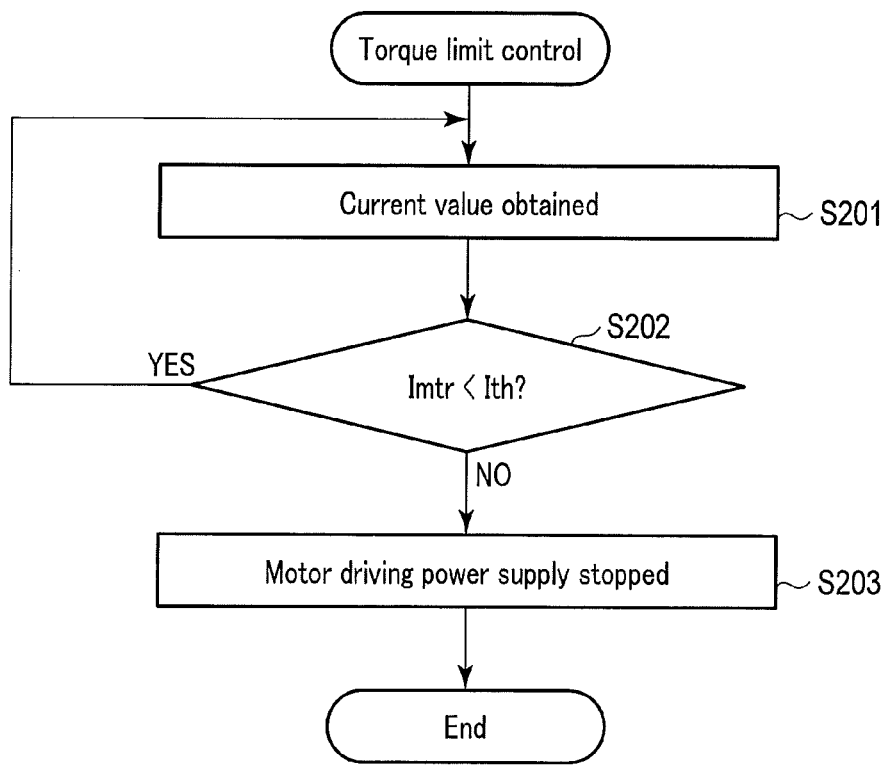
F I G. 5

INSERTION APPARATUS

CROSS-REFERENCE TO RELATED APPLICATIONS

This application is a Continuation Application of PCT Application No. PCT/JP2016/060473, filed Mar. 30, 2016 and based upon and claiming the benefit of priority from the prior Japanese Patent Application No. 2015-075410, filed Apr. 1, 2015, the entire contents of both of which are incorporated herein by reference.

BACKGROUND OF THE INVENTION

1. Field of the Invention

The present invention relates to a rotary self-propelled type insertion apparatus.

2. Description of the Related Art

Generally, an insertion apparatus such as an endoscope apparatus is inserted into a lumen. Among these types of insertion apparatuses, an insertion apparatus which is called a rotary self-propelled type has been known. The rotary self-propelled type endoscope apparatus is provided, for example, with a rotational housing which is called a spiral tube, etc. in which a spiral-shaped fin is formed on an outer peripheral surface of the insertion section. When the rotating housing is rotated, the fin formed to the rotational housing is brought into contact with an inner wall of a lumen, and generates friction. The insertion section self-propels in an insertion direction or in a removal direction by the friction. For example, Jpn. Pat. Appln. KOKAI Publication No. 2014-064686 provides suggestions regarding these types of self-propelled insertion apparatuses.

BRIEF SUMMARY OF THE INVENTION

An insertion apparatus according to an aspect of the invention comprises: an insertion section having an elongated shape; a rotational housing provided on an outer peripheral surface of the insertion section to be rotatable about a longitudinal axis; a motor that rotates the rotational housing; a drive control unit that supplies a driving current to the motor to control driving of the motor; a driving current detector that detects the driving current flowing through the motor; a torque limit value storage unit that stores a torque limit value which is an upper limit value of the driving current; a temperature detector provided in the rotational housing that detects a temperature of the rotational housing; a temperature measurement unit that measures a temperature in a vicinity of the rotational housing based on a detection result obtained from the temperature detector; and a torque limit value correction unit that corrects the torque limit value in accordance with the temperature measured by the temperature measurement unit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view of a configuration of an endoscope system as an example of an insertion apparatus according to an embodiment of the present invention;

FIG. 2 is a cross-sectional view of an enlarged rotation section;

FIG. 3 is an example of a torque limit setting table;

FIG. 4 is a flowchart of rotation control;

FIG. 5 is a flowchart of torque limit control; and

DETAILED DESCRIPTION OF THE INVENTION

Figure 6:
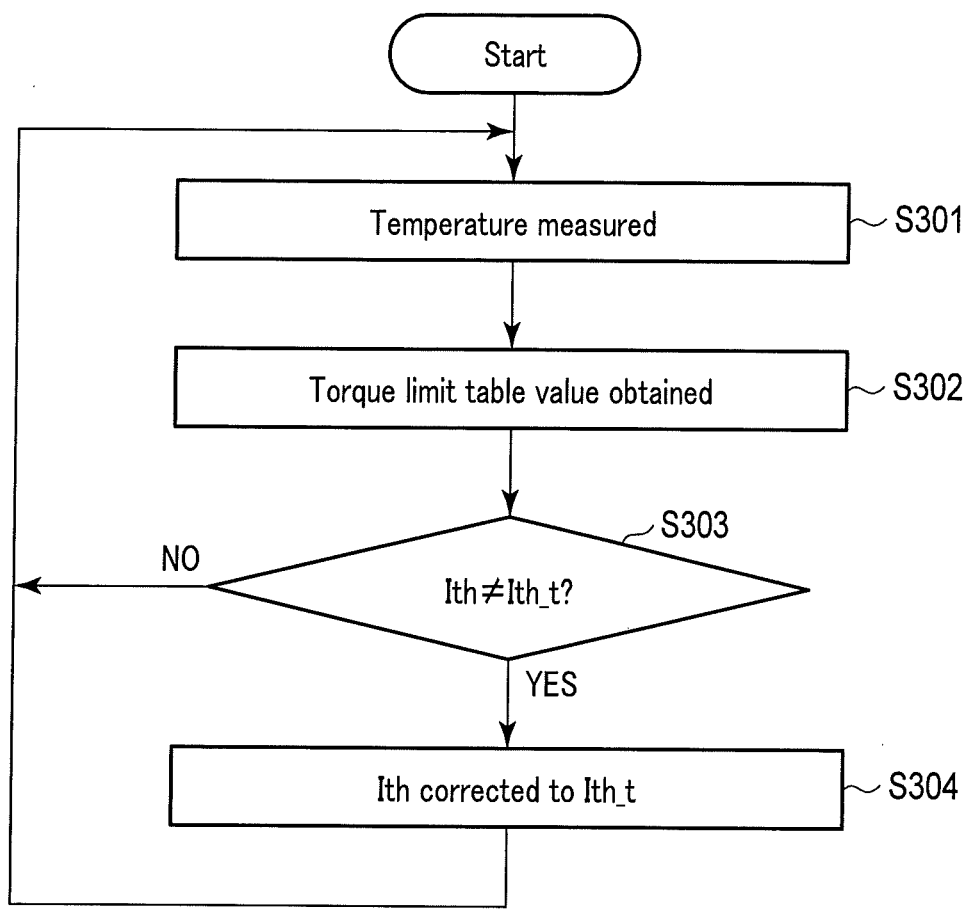
FIG. 6 is a flowchart of correction control for torque limit values.

Hereinafter, an embodiment of the present invention will be described with reference to the drawings. FIG. 1 is a schematic view of a configuration of an endoscope system as an example of an insertion apparatus according to an embodiment of the present invention. As shown in FIG. 1, an endoscope system 1 includes an endoscope 100, a controller 200, and a rotation operation unit 360.

The endoscope 100 is a rotary self-propelled type endoscope, and includes an insertion section 110. The insertion section 110 is an elongated shape, and is configured to be inserted into a body. The endoscope 100 also includes an operation unit 160 attached to the insertion section 110, by which various operations for the endoscope 100 are performed. The operation unit 160 is held by a user. The operation unit 160 of the endoscope 100 and the controller 200 are connected by a universal cable 190. In the following explanation, the side of a distal end of the insertion section 110 is referred to as a distal end side. The side of the insertion section 110 at which the operation unit 160 is provided is referred to as a proximal end side. The direction from the distal end to the proximal end of the insertion section 110 is referred to as a longitudinal direction.

The insertion section 110 includes a distal end hard section 112, a bending section 114, and a coiled hose section 116. The distal end hard section 112 is an edge of the distal end of the insertion section 110, and is formed to not be bent.

The distal end hard section 112 includes an imaging element 120. The imaging element 120 generates an image signal based on a subject image at the distal end side of the insertion section 110, for example. The image signal generated by the imaging element 120 is transmitted to an image processor 201 of the controller via an image signal line passing through the insertion section 110 and the universal cable 190. The bending section 114 is formed at the proximal end side of the distal end hard section 112, and is formed to be actively bent in accordance with an operation of an operation member (not shown in the drawings) provided to the operation unit 160. The coiled hose section 116 is formed at the proximal end side of the bending section 114, and is formed to be passively bent by external force.

The coiled hose section 116 is provided with a rotation section 130. The rotation section 130 is provided with a spiral tube 132 which is a rotational housing at the distal end. FIG. 2 is a cross-sectional view of the enlarged rotation section 130. As shown in FIG. 2, the rotation section 130 includes a housing 130a, a drive gear 130b, a drive shaft 130c, and a rotation transmission rubber 130d. The housing 130a is a cylindrical housing, and rotates in accordance with the rotation of a motor 150 built in the operation unit 160. The drive gear 130b is engaged with the housing 130a. The drive gear 130b transmits a driving power of the motor 150 transmitted from the drive shaft 130c to the housing 130a. The drive shaft 130c is connected to the motor 150, so as to rotate in accordance with the rotation of the motor 150, and to transmit the driving power of the motor 150 to the drive gear 130b. The rotation transmission rubber 130d has a cylindrical shape that covers an exterior of the housing 130a, and is a driving power transmission member that rotates in accordance with the rotation of the housing 130a and transmits the driving power of the motor 150 to the spiral tube 132.

The spiral tube 132 is formed of a soft material such as a rubber or a resin, for example, in a tubular shape. The spiral tube 132 is provided with a spiral fin 134 along the longitudinal axis of the spiral tube 132 on the outer peripheral surface. The spiral tube 132 may be configured to be removable from the rotation section 130.

A temperature sensor 118 that functions as a temperature detector is provided in the vicinity of the rotation section 130. The temperature sensor 118 is a sensor that detects the temperature inside of the rotation section 130, and preferably detects the temperature of the rotation transmission rubber 130d of the rotation section 130. An output signal of the temperature sensor 118 is transmitted to a temperature measurement unit 204 of the controller 200 through a sensor signal line passing through the insertion section 110 and the universal cable 190. For example, a contact type temperature sensor such as a thermocouple or a thermistor, or a non-contact type temperature sensor such as a radiation thermometer may be adopted as the temperature sensor 118. The contact type temperature sensor is disposed to be in contact with the rotation transmission rubber 130d, as shown in FIG. 2. The non-contact type temperature sensor is disposed in the vicinity of the rotation transmission rubber 130d. The temperature sensor 118 according to the present embodiment is not limited to a sensor having a particular structure, as long as it can detect the temperature of the vicinity of the rotation transmission rubber 130d. In an example shown in FIG. 2, the temperature sensor 118 is arranged to measure the temperature at a point of the rotation transmission rubber 130d. However, the temperature sensor 118 may be arranged to measure the temperature at multiple points of the rotation transmission rubber 130d. In this case, the average of the temperature measured at the multiple points, for example, is assumed to be the temperature of the rotation transmission rubber 130d.

The rotation section 130 is connected to the motor 150. The motor 150 is connected to the drive control unit 202 of the controller 200 via an actuator current signal line passing through the operation unit 160 and the universal cable 190.

The motor 150 operates by an operation using the rotation operation unit 360. The rotation power of the motor 150 is transmitted to the rotation section 130. As a result, the fin 134 provided in the spiral tube 132 rotates around the longitudinal axis. If the fin 134 rotates in the state of being in contact with a wall part such as an inner paries of a lumen, friction is generated to allow the insertion section 110 to self-propel. For example, in a small intestine or a large intestine, if the fin 134 is in contact with folds in the inner paries of the small intestine or the large intestine, friction is applied to the insertion section 110. The insertion section 110 self-propels by the friction. The self-propelling of the insertion section 110 assists the insertion operation or the removal operation of the insertion section 110 by the user. The motor 150 includes a pulse generator. The pulse generator generates a pulse signal (rotational speed signal) in accordance with the rotational speed of the motor 150, and inputs the rotational speed signal to the controller 200 via a rotational speed signal line passing through the universal cable 190. The rotational speed of the motor 150 is controlled by the rotational speed signal.

The rotation operation unit 360 may be a footswitch, for example. The footswitch includes a pedal on which a user steps, and generates a command signal in accordance with a pressure amount applied to the pedal.

The controller 200 controls each element of the endoscope system 1. The controller 200 includes an image processor 201, a drive control unit 202, a torque limit value storage unit 203, a temperature measurement unit 204 and a torque limit value correction unit 205.

The image processor 201 performs image processing to an image signal input to the image processor 201 through the insertion section 110 and the universal cable 190. The image processor 201 inputs the processed image signal to the display unit not shown in the drawings to display an endoscope image on the display unit.

The drive control unit 202 is configured, for example, by an ASIC, and acquires a command signal generated at the rotation operation unit 360 to obtain a command value. The drive control unit 202 includes a drive current detector 2021, and obtains a driving current value of the motor 150. The drive control unit 202 then generates a driving power based on the command value. The drive control unit 202 further supplies the driving power to the motor 150 to drive the motor 150. The drive control unit 202 compares the driving current value with a torque limit value stored in the torque limit value storage unit 203, and stops the rotation of the motor 150 when the driving current reaches or exceeds the torque limit value. By the torque limit function, the generation of excessive torque by the motor 150 is suppressed. Accordingly, it is possible to reduce a possibility of applying unnecessary force to the inner paries of a lumen.

The torque limit value storage unit 203 stores a torque limit value which is a threshold of a driving current to activate the torque limit function. The torque limit value storage unit 203 is formed, for example, of a nonvolatile memory.

The temperature measurement unit 204 measures the temperature of the rotation section 130 based on an output of the temperature sensor 118. For example, the temperature measurement unit 204 acquires a signal generated proportionally to the temperature detected by the temperature sensor 118, and converts the acquired signal into a temperature.

The torque limit value correction unit 205 includes a torque limit setting table 2051. The torque limit value correction unit 205 obtains a torque limit value Ith_t corresponding to the temperature measured at the temperature measurement unit 204 from the torque limit setting table 2051, and overwrites the setting of the torque limit value storage unit 203. Generally, the hardness of rubber changes due to a change in temperature. For example, the rubber used for the rotation transmission rubber 130d becomes softer at body temperature (approximately 36° C.) than at room temperature (approximately 20° C.). As the rotation transmission rubber 130d becomes softer, it becomes easier for the spiral tube 132 to be rotated by the rotation of the motor 150. Accordingly, even if the spiral tube 132 is rotated to the degree where the torque limit function has to be activated, there is a possibility that the torque limit function may not be enabled because the driving current falls below the torque limit value. In consideration of the above, in the present embodiment, the torque limit function is activated under the same conditions, regardless of the temperature of the rotation transmission rubber 130d, by correcting the torque limit value depending on the temperature inside the rotation section 130, and more preferably, the temperature of the rotation transmission rubber 130d of the rotation section 130. The torque limit setting table 2051 is a table that stores the relationships between the temperature and the torque limit value.

FIG. 3 is an example of the torque limit setting table 2051. As shown in FIG. 3, the torque limit setting table 2051 is a table in which the torque limit values Ith_t are associated with the temperatures in preset measurement points every 0.5° C. or 1° C. The torque limit value Ith_t of the torque limit setting table 2051 is obtained by actual measurement, for example, and the values shown in FIG. 3 are merely an example. The torque limit value Ith_t at a particular temperature between the measurement points shown in FIG. 3 is calculated by an interpolation operation using torque limit values Ith_t at two closest measurement points that are lower or higher than the temperature.

In the example shown in FIG. 1, the torque limit setting table is provided in the controller 200. Alternatively, the torque limit setting table may be provided in the endoscope 100.

Next, the operation of the endoscope system 1 according to the present embodiment will be explained. FIG. 4 is a flowchart of rotation control of the motor 150 of the endoscope 100. FIG. 5 is a flowchart of torque limit control. FIG. 6 is a flowchart of correction control for torque limit values. The controls of FIGS. 4, 5 and 6 are performed asynchronously, for example. Of course, the controls of FIGS. 4, 5, and 6 may be performed synchronously.

First, the rotation control will be explained with reference to FIG. 4. The operation shown in FIG. 4 is performed by the drive control unit 202. For example, the operation shown in FIG. 4 is initiated when the rotation operation unit 360 of the endoscope system 1 is operated. In step S101, the drive control unit 202 receives a command signal from the rotation operation unit 360, and generates a command value for the rotational speed in accordance with the pressing amount of the pedal of the rotation operation unit 360 by the user, based on the command signal.

In step S102, the drive control unit 202 receives a rotational speed signal from the pulse generator of the motor 150, and obtains the current value of the rotational speed based on the rotational speed signal.

In step S103, the drive control unit 202 generates a rotational speed signal in accordance with the deviation between the command value and the current value. The drive control unit 202 supplies the generated rotational speed signal to the motor 150 to drive the motor 150. Subsequently, the processing returns to step S101.

Next, the torque limit control will be explained with reference to FIG. 5. The operation shown in FIG. 5 is performed by the drive control unit 202. For example, the operation shown in FIG. 5 is initiated when the rotation control shown in FIG. 4 is initiated. In step S201, the drive control unit 202 obtains a current driving current value Imtr.

In step S202, the drive control unit 202 compares the driving current value Imtr and the current torque limit value Ith stored in the torque limit value storage unit 203, and determines whether Imtr is lower than Ith (Imtr<Ith). In step S202, if it is determined that Imtr<Ith is satisfied, the processing returns to step S201. In step S202, if it is determined that Imtr<Ith is not satisfied, the processing proceeds to step S203.

In step S203, the drive control unit 202 enables the torque limit function by stopping supply of the driving power to the motor 150. Then, the processing is terminated. After the torque limit function is activated, if the pressing upon the pedal is released, for example, the torque limit function is deactivated. After the torque limit function is deactivated, if the pedal is pressed again, the processing shown in FIG. 5 is resumed.

Next, the torque limit correction control will be explained with reference to FIG. 6. The operation shown in FIG. 6 is performed by the temperature measurement unit 204 and the torque limit value correction unit 205. For example, the operation shown in FIG. 6 is initiated when the endoscope system 1 is powered on. In step S301, the temperature measurement unit 204 measures the temperature of the rotation transmission rubber 130d based on an output of the temperature sensor 118.

In step S302, the torque limit value correction unit 205 obtains a torque limit value Ith_t in accordance with the temperature measurement result, from the torque limit setting table 2051.

In step S303, the torque limit value correction unit 205 determines whether the torque limit value Ith stored in the torque limit value storage unit 203 is different from the torque limit value Ith_t obtained in step S302. In step S303, if it is determined that the torque limit value Ith is not different from the torque limit value Ith_t, the processing returns to step S301. In this case, the torque limit control of FIG. 5 is performed with the torque limit value Ith that has been stored in the torque limit value storage unit 203. In step S303, if it is determined that the torque limit value Ith is different from the torque limit value Ith_t, the processing proceeds to step S304. In step S304, the torque limit value correction unit 205 performs correction to replace the torque limit value Ith with the torque limit value Ith_t. Subsequently, the processing returns to step S301. In this case, the torque limit control of FIG. 5 is performed with the replaced torque limit value Ith.

As explained above, according to the present embodiment, the torque limit value is corrected in accordance with the temperature in the vicinity of the spiral tube 132 so that the torque limit function is enabled in the state where the same load is actually applied to the spiral tube 132 regardless of the temperature of the rotation section 130.

[Modification]

A modification of the present embodiment will be explained below. In the aforementioned embodiment, the torque limit value is corrected by referring to the table. However, the correction of torque limit value may be performed without referring to the table. For example, if the temperature t and the torque limit value Ith_t can be approximated to a predetermined approximate expression (for example, a linear equation), the torque limit value correction unit 205 may be configured to perform correction using the linear equation instead of the table.

The present invention has been explained based on the embodiment; however, the present invention is not limited to the embodiment. The present invention may, of course, be modified in various ways without departing from the spirit and scope of the invention. In addition, the terms "first" or "next" are used for the explanation of the flowchart showing each operation; however, the sequence of the operation is not limited by these terms.

The operations described in the above embodiment may be stored in the form of programs executable by a CPU (which is a computer) or the like. The programs can be stored and distributed in storage mediums of external storage devices, such as a memory card, a magnetic disk, an optical disk, or a semiconductor memory. The CPU or the like reads the programs from a storage medium of an external storage device, and the operations can be executed and controlled based on the read programs.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
    an insertion section having an elongated shape;
    a rotational housing provided on an outer peripheral surface of the insertion section to be rotatable about a longitudinal axis;
    a motor that rotates the rotational housing;
    a drive control unit that supplies a driving current to the motor to control driving of the motor;
    a driving current detector that detects the driving current flowing through the motor;
    a torque limit value storage unit that stores a torque limit value which is an upper limit value of the driving current;
    a temperature measurement unit that measures a temperature in a vicinity of the rotational housing; and
    a torque limit value correction unit that corrects the torque limit value in accordance with the temperature measured by the temperature measurement unit.

2. The insertion apparatus according to claim 1, further comprising a temperature detector provided in the rotational housing that detects a temperature of the rotational housing.

3. The insertion apparatus according to claim 2, comprising a rotation section that transmits a driving power of the motor to the rotational housing,
    wherein the temperature detector detects a temperature of the rotation section.

4. The insertion apparatus according to claim 3, wherein a driving power transmission member formed of rubber is provided between the rotation section and the rotational housing.

5. The insertion apparatus according to claim 2, wherein the temperature detector detects a temperature at a plurality of points of the rotational housing.

6. The insertion apparatus according to claim 1, wherein the drive control unit stops rotation of the motor when the driving current reaches or exceeds a predetermined torque limit value.

* * * * *